United States Patent
Hoff et al.

(10) Patent No.: US 9,946,820 B2
(45) Date of Patent: Apr. 17, 2018

(54) METHOD AND SIMULATION SYSTEM FOR CREATING A SIMULATION ENVIRONMENT OF A MEDICAL IMAGING DEVICE

(71) Applicant: Siemens Aktiengesellschaft, Munich (DE)

(72) Inventors: Maart Hoff, Erlangen (DE); Marcus Wuebbe, Herzogenaurach (DE)

(73) Assignee: Siemens Aktiengesellschaft, Munich (DE)

( * ) Notice: Subject to any disclaimer, the term of this patent is extended or adjusted under 35 U.S.C. 154(b) by 397 days.

(21) Appl. No.: 14/735,533

(22) Filed: Jun. 10, 2015

(65) Prior Publication Data

US 2015/0356216 A1     Dec. 10, 2015

(30) Foreign Application Priority Data

Jun. 10, 2014   (DE) .................. 10 2014 211 044

(51) Int. Cl.
  *G06F 17/50*   (2006.01)
  *G06F 19/00*   (2011.01)

(52) U.S. Cl.
  CPC ........ *G06F 17/5009* (2013.01); *G06F 19/321* (2013.01); *G06F 19/3412* (2013.01)

(58) Field of Classification Search
  USPC ................ 703/20, 22; 382/131; 348/340
  See application file for complete search history.

(56) References Cited

U.S. PATENT DOCUMENTS

| | | | |
|---|---|---|---|
| 7,577,722 B1 | 8/2009 | Khandekar et al. | |
| 7,680,314 B2* | 3/2010 | Hong | G06T 7/143 382/131 |
| 8,924,864 B2* | 12/2014 | Mariotti | G06F 19/321 715/753 |
| 8,928,796 B2* | 1/2015 | Van Heugten | H04N 5/2254 348/340 |
| 9,560,318 B2* | 1/2017 | Reina | G06T 9/001 |
| 2013/0282117 A1* | 10/2013 | Van Heugten | A61F 2/1624 623/6.22 |
| 2013/0339958 A1* | 12/2013 | Droste | G06F 21/41 718/1 |

OTHER PUBLICATIONS

Santos et al., "Flexible Real-Time Magnetic Resonance Imaging Framework"; Engineering in Medicine and Biology Society, 26th Annual International Conference of the IEEE, pp. 1048-1051, ( 2004).

* cited by examiner

*Primary Examiner* — Thai Phan
(74) *Attorney, Agent, or Firm* — Schiff Hardin LLP

(57) ABSTRACT

In a method and a computer-readable storage medium for creating a simulation environment for a simulation system of a medical imaging device by a server unit, as well as a server unit and a simulation system for implementing such a method, after reading in an event protocol of the medical imaging device, a determination of a software configuration of the medical imaging device takes place with the use of the event protocol and a determination of a memory image that corresponds to the software configuration of the medical imaging device. The determined memory image can be transferred to the simulation system and the read-in event protocol transferred to the simulation system.

7 Claims, 1 Drawing Sheet

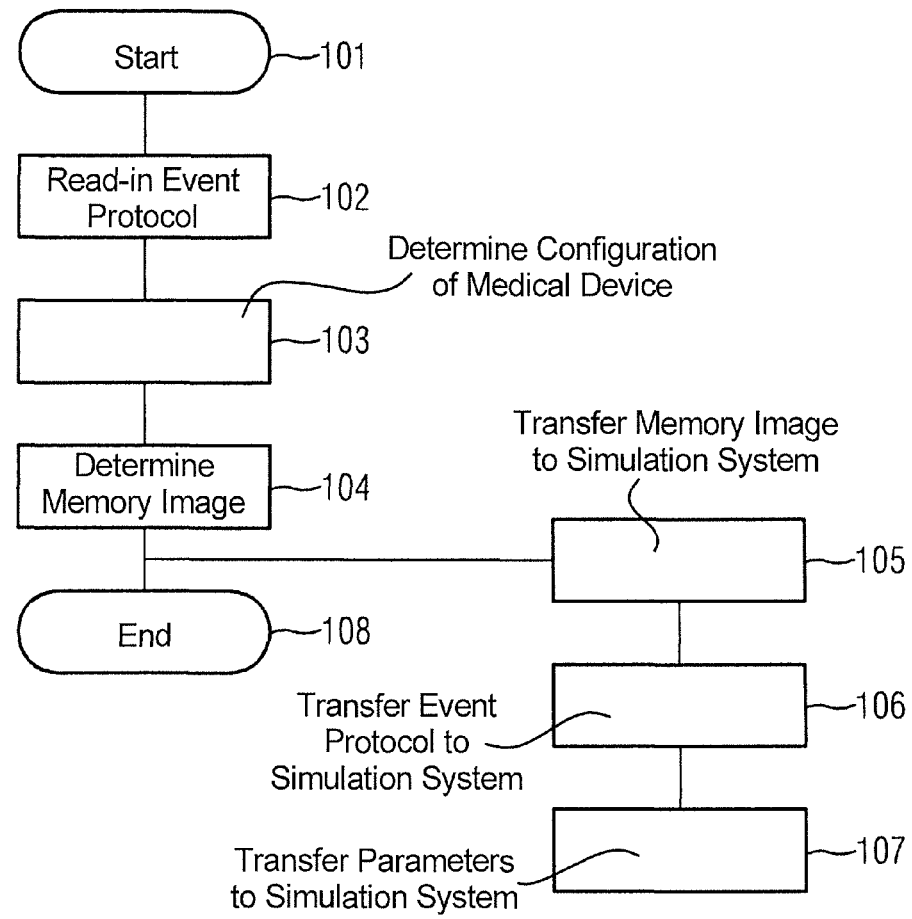
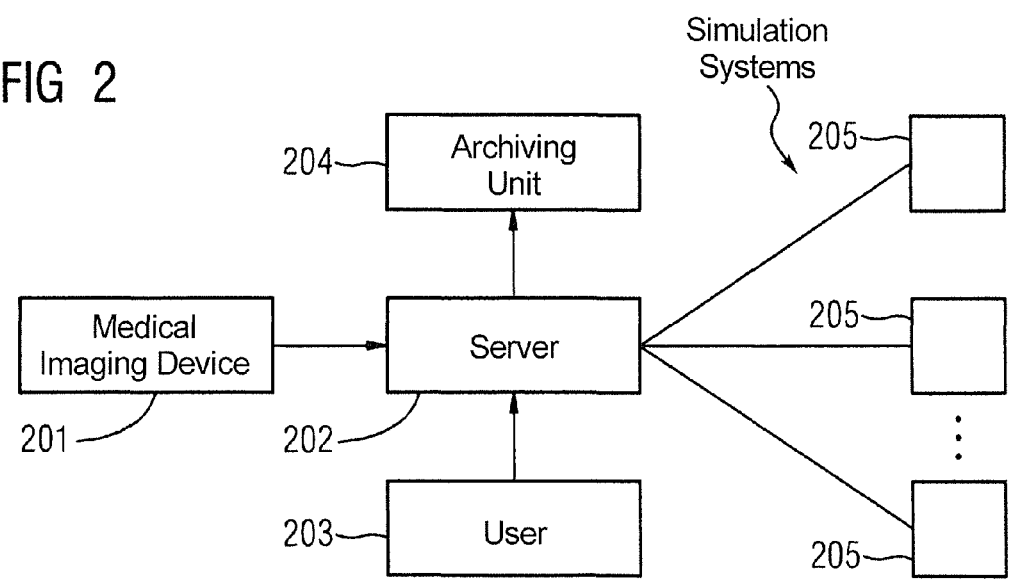

METHOD AND SIMULATION SYSTEM FOR CREATING A SIMULATION ENVIRONMENT OF A MEDICAL IMAGING DEVICE

BACKGROUND OF THE INVENTION

Field of the Invention

The present invention relates to a method for creating a simulation environment for a simulation system of a medical imaging device via a server unit, as well as a corresponding electronically readable data storage medium and a server unit and simulation system.

Description of the Prior Art

Medical imaging devices for displaying examination objects are in widespread use in clinical applications.

Medical imaging devices are complex systems, during the operation of which various incidents or faults, also referred to below as events, may sometimes occur. In order to analyze these events, it is usual for the creation of a fault protocol to be triggered by the user and the event is mapped within a simulation environment.

SUMMARY OF THE INVENTION

An object of the invention is to provide a method that allows a memory image of a medical imaging device, which concerns an event or is specific to this event, to be determined, so analysis of the event is simplified.

This object is achieved in accordance with the invention by a method for creating a simulation environment for a simulation system of a medical imaging device using a server unit, that includes reading an event protocol of the medical imaging device into the server, determining a software configuration of the medical imaging device in the server with the use of the event protocol, as well as determining a memory image corresponding thereto, and storing the memory image corresponding to the software configuration of the medical imaging device in an archive unit.

A medical imaging device is a device, preferably an electronic and/or IT device, for capturing, processing, evaluating and/or storing image information in the form of image data. To capture the image information, it is possible for example to use acoustic methods such as ultrasound (US), emission methods such as emission computed tomography (ECT) and positron emission tomography (PET), optical methods, and radiological methods such as X-ray tomography and computed tomography (CT), but the capture can also take place using magnetic resonance tomography (MR or MRT) or nuclear spin tomography or using combined methods. The medical imaging device may supply 2-dimensional (2D) or multidimensional image data, for instance 3-dimensional (3D) or 4-dimensional (4D), which are preferably stored and/or processed in different formats. The medical imaging device can be used in diagnostics, for example in medical diagnostics.

An event may be any type of incident and/or fault, such as can occur during operation of the medical imaging device. An event may also be a previously defined special feature, the occurrence of which is to be determined and/or recorded. An event protocol may include for instance a savelog, in which information relating to the installed software and/or the measured protocols is inter alia stored.

A simulation system is a computer in which an imaging device is recreated for simulation purposes, on which effects of various settings can be tested and/or mapped. A simulation environment is the software configuration required for the simulation system.

A memory image is a specific software configuration for instance at a specific point in time or for a specific device and/or for a specific measurement protocol.

An archive unit is understood to mean a memory unit, in which a multiple of different memory images are kept available.

The method for creating the simulation environment for the simulation system of the medical imaging device by operation of the server unit finally results in the determination of a memory image corresponding to the software configuration of the medical image device and storing the memory image in the archive unit.

The invention uses a generated and/or existing event protocol of the medical imaging device in order to determine a software configuration of the medical imaging device and to determine a memory image that corresponds to the software configuration of the medical imaging device. The direct determination of a memory image of this type allows the software configuration underlying the generation of the event protocol, and as a result possibly the software configuration causing the generation of the event protocol, to be defined in a time-saving manner.

In a preferred embodiment, the determined memory image is transferred to the simulation system. In this way, the determination can also include an installation of the corresponding memory image on the simulation system. This option of determining a memory image from an event protocol and of configuring a corresponding simulation system therefrom dispenses with the need to retain multiple different simulation systems. This reduces costs for hardware as well as for power consumption. A suitable simulation system can thus be installed for a corresponding event protocol in a short period of time and with little outlay.

In an embodiment, the read-in event protocol is transferred to the simulation system. As a result, additional information can be transferred to the simulation system and the underlying event can be examined and/or reproduced more precisely.

In a further embodiment, parameters stored in the transmitted event protocol are transferred to a virtual environment of the simulation system. Here stored parameters are understood to mean, for instance, coil configurations used in magnetic resonance devices, said coil configurations being mapped on a virtual environment, in this example on virtual coils, in order to simulate the underlying device precisely. Here virtual environment is understood to mean a virtual instance of a specific hardware composition.

In a preferred embodiment, the medical imaging device is formed by a magnetic resonance device.

Within the scope of the present invention, a server unit is also provided to create a simulation environment for a simulation system of a medical imaging device and a simulation system, including a server unit and a simulation system for creating a simulation environment for a simulation system of a medical imaging device. Here the actual server unit can be controlled and operated independently of the medical imaging device.

Further, the present invention encompasses a non-transitory computer-readable storage medium encoded with programming instructions (code), which can be loaded in a memory of a programmable controller or a computing unit of a medical imaging device. With the programming instructions, all or various previously described embodiments of the inventive method can be executed, when the run in the controller or control facility of the medical imaging device. In such cases the programming instructions may require other program items, e.g. libraries and auxiliary functions, in order to realize the corresponding embodiments of the method. The programming instructions may be a source code, which must still be compiled and be interpreted, or an executable software code, which is directly loaded for execution into the corresponding computing unit.

The computer-readable storage medium can be, for example, a DVD, a hard disk or a USB stick, on which electronically readable control information, in particular software, is stored.

The advantages of the inventive medical imaging device and the inventive computer-readable storage medium, and of the server unit and the simulation system correspond substantially to the advantages of the inventive method, as described in detail above. Features, advantages or alternative embodiments mentioned herein are applicable equally to all of the aspects of the invention. The functional features of the method are configured in the server and system suitable modules, in particular hardware modules.

BRIEF DESCRIPTION OF THE DRAWINGS

FIG. 1 is a flowchart of an embodiment of the inventive method.

FIG. 2 is a block diagram for creating a simulation environment with a server unit in accordance with the invention.

DESCRIPTION OF THE PREFERRED EMBODIMENTS

FIG. 1 is a flowchart of an embodiment of the method according to the invention. The method includes the method steps 101 to 108, wherein, when describing the method steps 101 to 108, description parts including the corresponding reference characters introduced in conjunction with those in FIG. 2 are also used.

The method steps 101 to 108 are implemented here by a server unit 202 in order to create a simulation environment for a simulation system 205 of a medical imaging device 201.

A first method step 101 designates the start of a creation of a simulation environment for a simulation system 205 of a medical imaging device 201 by means of a server unit 202.

In method step 102, a reading-in of an event protocol of the medical imaging device 201 takes place.

Method step 103 designates the determination of a software configuration of the medical imaging device 201 with the use of the event protocol. An event may be any type of incident or fault, such as can occur during operation of the medical imaging device 201. An event may however also be a previously defined special feature, the occurrence of which is to be defined and/or recorded. An event protocol may include for instance a savelog, in which information relating to the installed software and/or the measured protocols is inter alia stored.

In method step 104, a determination of a memory image corresponding to the software configuration of the medical imaging device 201 takes place in the server and it is provided to an archive unit 203. A memory image is a specific software configuration for instance at a specific point in time and/or for a specific device and/or for a specific measurement protocol.

Method step 105, an optional step following method step 104, identifies a transfer of the determined memory image on the simulation system 205. A memory image can thus be determined from an event protocol and a corresponding simulation system 205 can be configured therefrom.

Method step 106, an optional step following method step 105, designates a transfer of the read-in event protocol onto the simulation system 205. As a result, additional information can be transferred to the simulation system 205 and the underlying event can be examined and/or reproduced more precisely.

Method step 107, an optional step following method step 106, designated a transfer of parameters stored in the transmitted event protocol onto a virtual environment of the simulation system 205. Here stored parameters are understood to mean for instance coil configurations used in magnetic resonance devices, the coil configurations being mapped on a virtual environment, in this example on virtual coils, in order to simulate the underlying device precisely.

The last method step 108 designates the end of a creation of a simulation environment for a simulation system 205 of a medical imaging device 201 by means of a server unit 202.

FIG. 2 shows an exemplary block diagram for creating a simulation environment by a server unit 202.

Once an event protocol has been reported and/or created by a medical imaging device 201 and/or a user 203 of the medical imaging device 201, this is read in by the server unit 202. The server unit 202 also determines a software configuration of the medical imaging device 201 with the use of the event protocol. Determination of a memory image, which corresponds to the software configuration of the medical imaging device 201, takes place, and it is stored in an archive unit 204.

The determined memory image can then be installed on one or a number of simulation systems 205. The read-in event protocol can likewise be transferred to the simulation system 205. The parameters stored in the transmitted event protocol can be transferred to a virtual environment of the simulation system 205.

The medical imaging device 201 shown here is a magnetic resonance device, the imaging device 201 may however also be for instance a positron emission tomography device, a computed tomography device or a combined device.

Although the invention has been illustrated and described in greater detail on the basis of the preferred exemplary embodiments, the invention is not limited by the disclosed examples. Variations can be derived therefrom by those skilled in the art without departing from the scope of the invention.

In summary, the invention relates to a method and a computer-readable storage medium for creating a simulation environment for a simulation system of a medical imaging device by a server unit, as well as a server unit and a simulation system for implementing such a method. After reading in an event protocol of the medical imaging device, a determination of a software configuration of the medical imaging device takes place with the aid of the event protocol and a determination of a memory image which corresponds to the software configuration of the medical imaging device. In a preferred embodiment, the determined memory image is transferred to the simulation system and the read-in event protocol is transferred to the simulation system.

We claim as our invention:
1. A method for generating a simulation environment for a simulation system that simulates operation of a medical imaging device comprising:
   via a server in communication with said medical imaging device, reading an event protocol of the medical imaging device into the server said event protocol describing events that occurred during operation of the medical imaging while conducting a medical procedure involving medical imaging by the medical imaging device;

in the server, using the event protocol to determine a software configuration of the medical imaging device that controlled the operation of the medical imaging device during said medical procedure;

in the server, generating a memory image corresponding to the software configuration of the medical imaging device;

transferring said memory image from said server to an archive memory; and transferring said memory image from said archive memory to a simulation system and, in said simulation system, using said memory image to generate a simulated environment of said medical imaging device that existed during said medical procedure.

2. A method as claimed in claim 1 comprising also transferring said read-event protocol from said medical imaging device to said at least one simulation system via said server.

3. A method as claimed in claim 2 comprising transferring parameters stored in the transmitted event protocol to a virtual environment in the at least one simulation system.

4. A method as claimed in claim 1 wherein said medical imaging device is a magnetic resonance device.

5. A server for generating a simulation environment for a simulation system that simulates operation of a medical imaging device, said server being configured to:

read an event protocol of the medical imaging device into the server said event protocol describing events that occurred during operation of the medical imaging while conducting a medical procedure involving medical imaging by the medical imaging device;

use the event protocol to determine a software configuration of the medical imaging device that controlled the operation of the medical imaging device during said medical procedure;

generate a memory image corresponding to the software configuration of the medical imaging device; and transfer said memory image from said server to an archive memory.

6. A simulation system for generating a simulation environment for a simulation system that simulates operation of a medical imaging device comprising:

a server in communication with said medical imaging device configured to read an event protocol of the medical imaging device into the server said event protocol describing events that occurred during operation of the medical imaging while conducting a medical procedure involving medical imaging by the medical imaging device;

said server being configured to use the event protocol to determine a software configuration of the medical imaging device that controlled the operation of the medical imaging device during said medical procedure;

said server being configured to generate a memory image corresponding to the software configuration of the medical imaging device;

said server being configured to transfer said memory image from said server to an archive memory; and a simulation system processor configured to access said archive memory in order to retrieve said memory image therefrom, and to use said memory image to generate simulated environment of said medical imaging device that existed during said medical procedure.

7. A non-transitory, computer-readable data storage medium encoded with programming instructions, said storage medium being distributively loaded into a server and a simulation system processor, and said storage medium being encoded with programming instructions and said programming instructions causing said server and said simulation system processor to:

read an event protocol of a medical imaging device into the server said event protocol describing events that occurred during operation of the medical imaging while conducting a medical procedure involving medical imaging by the medical imaging device;

in the server, use the event protocol to determine a software configuration of the medical imaging device that controlled the operation of the medical imaging device during said medical procedure;

in the server, generate a memory image corresponding to the software configuration of the medical imaging device;

transfer said memory image from said server to an archive memory; and in said simulation system processor, access said archive memory in order to retrieve the memory image therefrom, and use the memory image to generate a simulated environment of the medical imaging device that existed during said medical procedure.

* * * * *